US007482464B2

(12) United States Patent
Chung et al.

(10) Patent No.: US 7,482,464 B2
(45) Date of Patent: Jan. 27, 2009

(54) PROCESSES FOR THE PREPARATION OF S-(-)-AMLODIPINE

(75) Inventors: You Sup Chung, Suwon (KR); Mun Choun Ha, Yongin (KR)

(73) Assignee: Hanlim Pharmaceutical Co., Ltd., Seoul (KR)

( * ) Notice: Subject to any disclaimer, the term of this patent is extended or adjusted under 35 U.S.C. 154(b) by 88 days.

(21) Appl. No.: 11/680,261

(22) Filed: Feb. 28, 2007

(65) Prior Publication Data

US 2007/0155969 A1 Jul. 5, 2007

Related U.S. Application Data

(62) Division of application No. 10/527,091, filed as application No. PCT/KR03/01849 on Sep. 8, 2003, now Pat. No. 7,202,365.

(30) Foreign Application Priority Data

Sep. 11, 2002 (KR) ............... 10-2002-0054808

(51) Int. Cl.
*C07D 213/82* (2006.01)
(52) U.S. Cl. .................................................. 546/321
(58) Field of Classification Search ............... 546/321
See application file for complete search history.

(56) References Cited

U.S. PATENT DOCUMENTS

2003/0176706 A1 * 9/2003 Joshi et al. ............... 546/315

FOREIGN PATENT DOCUMENTS

WO 95/25722 * 9/1995

* cited by examiner

*Primary Examiner*—Patricia L Morris
(74) *Attorney, Agent, or Firm*—Rothwell, Figg, Ernst & Manbeck

(57) ABSTRACT

Provided is a process for the preparation of S-(-)-amlodipine from (R,S)-amlodipine in industrial-scale using L-(+)-tartaric acid, which is much cheaper than D-(-)-tartaric acid.

1 Claim, 2 Drawing Sheets

PROCESSES FOR THE PREPARATION OF S-(−)-AMLODIPINE

CROSS REFERENCE TO RELATED APPLICATION

This application is a divisional of U.S. application Ser. No. 10/527,091, filed Mar. 9, 2005, now U.S. Pat. No. 7,202,365, which is a 35 U.S.C. § 371 National Phase Entry Application from PCT/KR03/001849, filed Sep. 8, 2003, and designating the U.S.

BACKGROUND OF THE INVENTION

1. Field of the Invention

The present invention relates to a process for the preparation of S-(−)-amlodipine, more specifically, to a process for the preparation of S-(−)-amlodipine from (R,S)-amlodipine in industrial-scale using L-(+)-tartaric acid, which is much cheaper than D-(−)-tartaric acid.

2. Description of the Related Art

Amlodipine, with a chemical name of 3-ethyl 5-methyl 2-[(2-aminoethoxy)methyl]-4-(2-chlorophenyl)-1,4-dihydro-6-methylpyridine-3,5-dicar boxylate, is a potent and long-acting calcium channel blocker useful as an anti-ischaemic and anti-hypertensive agent. It is known that two types of enantiomers of amlodipine have different pharmacological profiles. S-(−)-isomer is a more potent calcium channel blocker than R-(+)-isomer, while the R-(+)-isomer also exhibits an activity in the treatment or prevention of atherosclerosis.

J. Med. Chem. (1986) 29 1696 discloses a process for the preparation of the two enantiomers of amlodipine via separation of the diastereomeric azide esters, and EP 331,315 A1 discloses the use of cinchonidine salts for the resolution of intermediates to eventually give enantiomerically pure amlodipine isomers. J. Med. Chem. (1992) 35 3341 discloses a chromatographic separation of diastereomeric amide isomers.

Further, WO 95/25722 discloses a method for the separation of the (R)-(+)- and (S)-(−)-isomers of amlodipine from mixtures thereof, which comprises reacting the mixture of isomers with either L-(+)- or D-(−)-tartaric acid in dimethyl sulfoxide (DMSO) for the preparation of, respectively, a DMSO solvate of an L-tartrate salt of (R)-(+)-amlodipine, or a DMSO solvate of a D-tartrate salt of (S)-(−)-amlodipine.

In order to manufacture (S)-(−)-amlodipine, having a more potent calcium channel blocking activity, the process according to WO 95/25722 employs D-tartaric acid. However, the fact that D-(−)-tartaric acid is very expensive compared to L-(+)-tartaric acid is unfavorable for industrial-scale mass production of (S)-(−)-amlodipine.

Therefore, a method of industrial-scale mass production of (S)-(−)-amlodipine has been in demand.

SUMMARY OF THE INVENTION

The present invention provides a process for the preparation of S-(−)-amlodipine from (R,S)-amlodipine in industrial-scale using L-(+)-tartaric acid, which is much cheaper than D-(−)-tartaric acid.

Further, the present invention provides synthetic intermediates for the preparation of S-(−)-amlodipine.

In one aspect of the present invention, there is provided a process for the preparation of S-(−)-amlodipine, which comprises (i) reacting (R,S)-amlodipine with L-(+)-tartaric acid in dimethyl sulfoxide (DMSO); (ii) filtering off the resulting precipitate of step (i); (iii) precipitating (S)-(−)-amlodipine-hemi-L-tartrate-DMSO-solvate by adding methylene chloride to the filtrate of step (ii); (iv) optionally forming (S)-(−)-amlodipine-hemi-L-tartrate-monohydrate by adding an alcohol to (S)-(−)-amlodipine-hemi-L-tartrate-DMSO-solvate obtained in step (iii); and (v) treating with a base (S)-(−)-amlodipine-hemi-L-tartrate-DMSO-solvate obtained in step (iii) or (S)-(−)-amlodipine-hemi-L-tartrate-monohydrate obtained in step (iv).

In another aspect of the present invention, there is provided (S)-(−)-amlodipine-hemi-L-tartrate-DMSO-solvate or (S)-(−)-amlodipine-hemi-L-tartrate-monohydrate, each being useful for the preparation of S-(−)-amlodipine.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
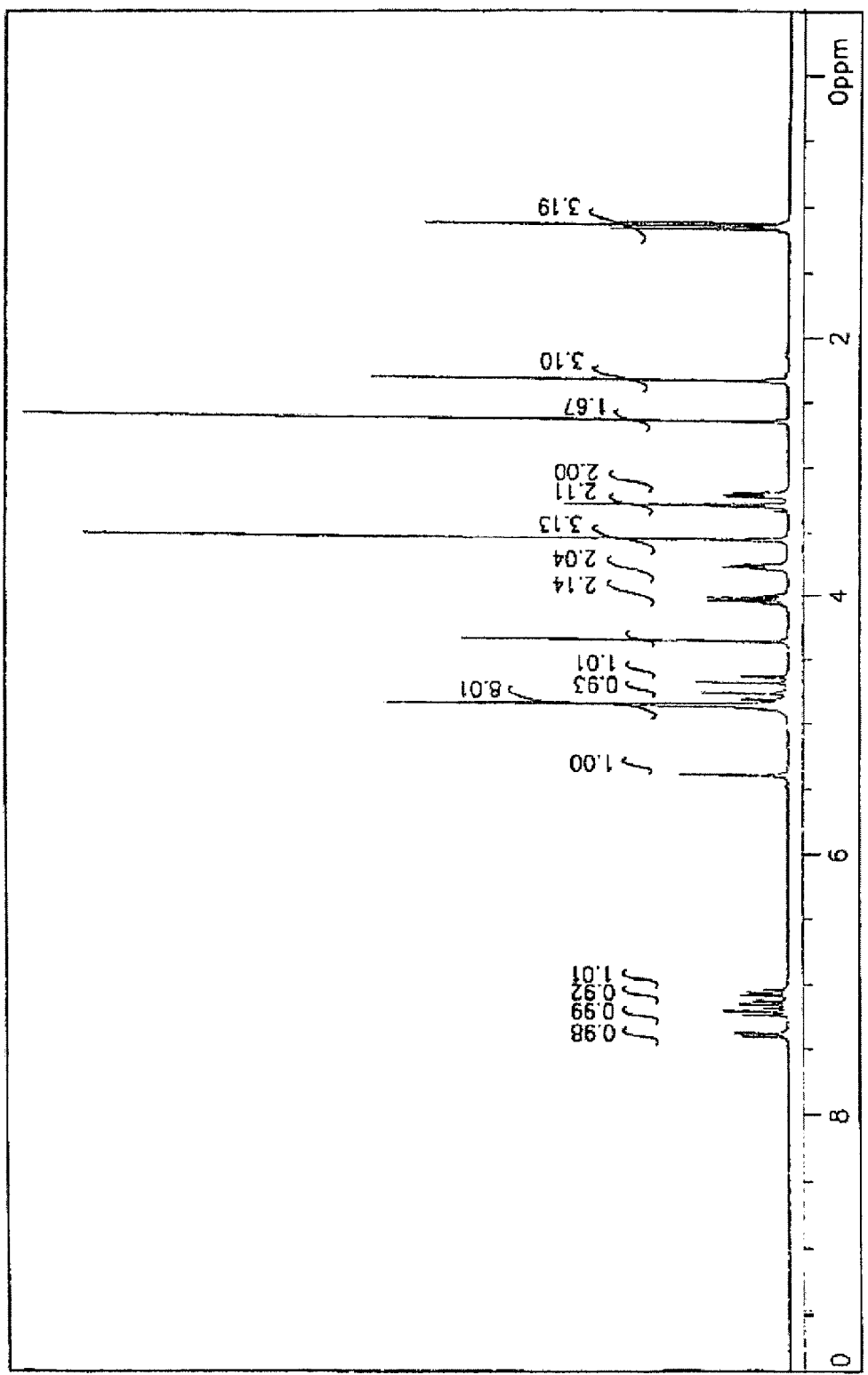
FIG. 1 shows a $^1$H-NMR chart of (S)-(−)-amlodipine-hemi-L-tartrate-DMSO-solvate.

The present invention provides an economic process for preparing S-(−)-amlodipine in high yield and enantiomeric purity. According to the process of the present invention, (R,S)-amlodipine is reacted with L-(+)-tartaric acid in dimethyl sulfoxide (DMSO) and the resulting precipitate is filtered off. The resultant filtrate is added with methylene chloride to precipitate (S)-(−)-amlodipine-hemi-L-tartrate-DMSO-solvate. Optionally, (S)-(−)-amlodipine-hemi-L-tartrate-DMSO-solvate is added with an alcohol to form (S)-(−)-amlodipine-hemi-L-tartrate-monohydrate. (S)-(−)-amlodipine-hemi-L-tartrate-DMSO-solvate or (S)-(−)-amlodipine-hemi-L-tartrate-monohydrate is treated with a base.

The following reaction scheme illustrates the process of the present invention.

Reaction Scheme:

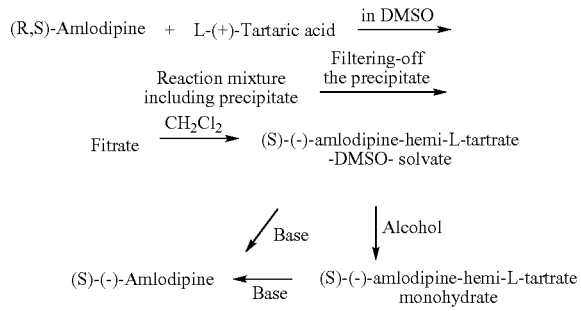

L-(+)-tartaric acid is much cheaper than D-(−)-tartaric acid, and greatly downs the production cost, which is very favorable for industrial-scale mass production of S-(−)-amlodipine. Preferably, the amount of L-(+)-tartaric acid is about 0.5~0.55 eq. to 1 eq. of (R,S)-amlodipine.

In one embodiment, (R,S)-Amlodipine is reacted with L-(+)-tartaric acid in dimethyl sulfoxide (DMSO) to give a precipitate, (R)-(+)-amlodipine-hemi-L-tartrate-DMSO-solvate, which is then filtered off. The amount of DMSO is about 4-6 times, preferably about 5 times, in volume (ml) to 1 gram of the racemic mixture, i.e., (R,S)-amlodipine. In case an excess of DMSO is used (e.g., about 10 ml of DMSO to 1 gram of (R,S)-amlodipine), about 10% of (R)-(+)-amlodipine-hemi-L-tartrate-DMSO-solvate may exist in DMSO, which unfavorably causes lowering the optical purity of the final product, i.e., (S)-amlodipine.

In filtering-off (R)-(+)-amlodipine-hemi-L-tartrate-DMSO-solvate, any conventional filtration methods can be used, preferably under a reduced pressure. For example, conventional centrifugation methods can be used. In this case, a supernatant obtained by the centrifugation is used as the filtrate in the subsequent step. Therefore, the filtering-off process according to the present invention should be construed to include any applicable conventional methods for removing a precipitate.

Addition of methylene chloride to the filtrate gives a precipitate, i.e., (S)-(−)-amlodipine-hemi-L-tartrate-DMSO-solvate. The amount of methylene chloride may be about 100-200% by volume based on the volume of DMSO used in the step (i).

The process of the present invention may further comprise a recrystallization step for forming (S)-(−)-amlodipine L-(+)-tartrate free from DMSO, i.e., (S)-(−)-amlodipine-hemi-L-tartrate-monohydrate. The optical purity of (S)-amlodipine may be increased by further performing the recrystallization step. The recrystallization may be performed using an alcohol, including methanol.

The process of the present invention comprises treating with a base (S)-(−)-amlodipine-hemi-L-tartrate-DMSO-solvate or (S)-(−)-amlodipine-hemi-L-tartrate-monohydrate to give optically pure (S)-(−)-amlodipine. The base includes, but not limited to, a metal hydroxide, an oxide, a carbonate, a bicarbonate, and an amide. Preferably, the base is sodium bicarbonate. Further, the treatment with a base may be performed in an organic solvent, preferably methylene chloride.

The present invention also includes, within its scope, synthetic intermediates for the preparation of S-(−)-amlodipine. That is, the present invention provides (S)-(−)-amlodipine-hemi-L-tartrate-DMSO-solvate or (S)-(−)-amlodipine-hemi-L-tartrate-monohydrate, each being useful for the preparation of S-(−)-amlodipine. (S)-(−)-amlodipine-hemi-L-tartrate-DMSO-solvate may be in a form of 1/4-, 1/2-(i.e., hemi-), or mono-DMSO solvate; or in a form of the mixture thereof, e.g., the mixture of 1/4- and 1/2-DMSO solvate. Preferably, (S)-(−)-amlodipine-hemi-L-tartrate-DMSO-solvate is the form of 1/4-DMSO solvate, i.e., (S)-(−)-amlodipine-hemi-L-tartrate-1/4-DMSO-solvate.

Although the present invention may be more detailed explained by reference to the following Examples, the following Examples are not intended to limit the scope of the present invention.

EXAMPLE 1

Preparation of S-(−)-amlodipine from (R,S)-amlodipine (1) (S)-(−)-amlodipine-hemi-L-tartrate-DMSO-solvate The solution of L-(+)-tartaric acid (1.872 g, 0.51 mole equivalents) in dimethyl sulfoxide (25 ml) was added to the solution of (R,S)-amlodipine (10 g, 24.46 mmole) in dimethyl sulfoxide (25 ml) under stirring. Precipitation was observed within 5 minutes after the addition, and the resulting slurry was stirred overnight at room temperature. The resulting solid was filtered off. $CH_2Cl_2$ (50 ml) was added to the obtained filtrate, which was then stirred at room temperature for 40 hours. The resulting slurry was cooled to 5° C., stirred for 2 hours, and then filtered. The resulting solid was dried overnight at 50° C. in vacuo to give a solid (5.48 g) having the following $^1$H-NMR data. FIG. 1 shows the $^1$H-NMR chart of the solid, which means that the solid is (S)-(−)-amlodipine-hemi-L-tartrate-1/4-DMSO-solvate.

$^1$H-NMR (CD$_3$OD): 7.04-7.41 (m, 4H), 5.40 (s, 1H), 4.72 (gq, 2H), 4.36 (s,1H) 4.02 (m, 2H), 3.77 (m, 2H), 3.57 (s, 3H), 3.28 (m, 2H), 2.65 (s, DMSO), 2.31 (s, 3H), 1.15 (t, 3H)

(2) (S)-(−)-amlodipine-hemi-L-tartrate-monohydrate

Figure 2:
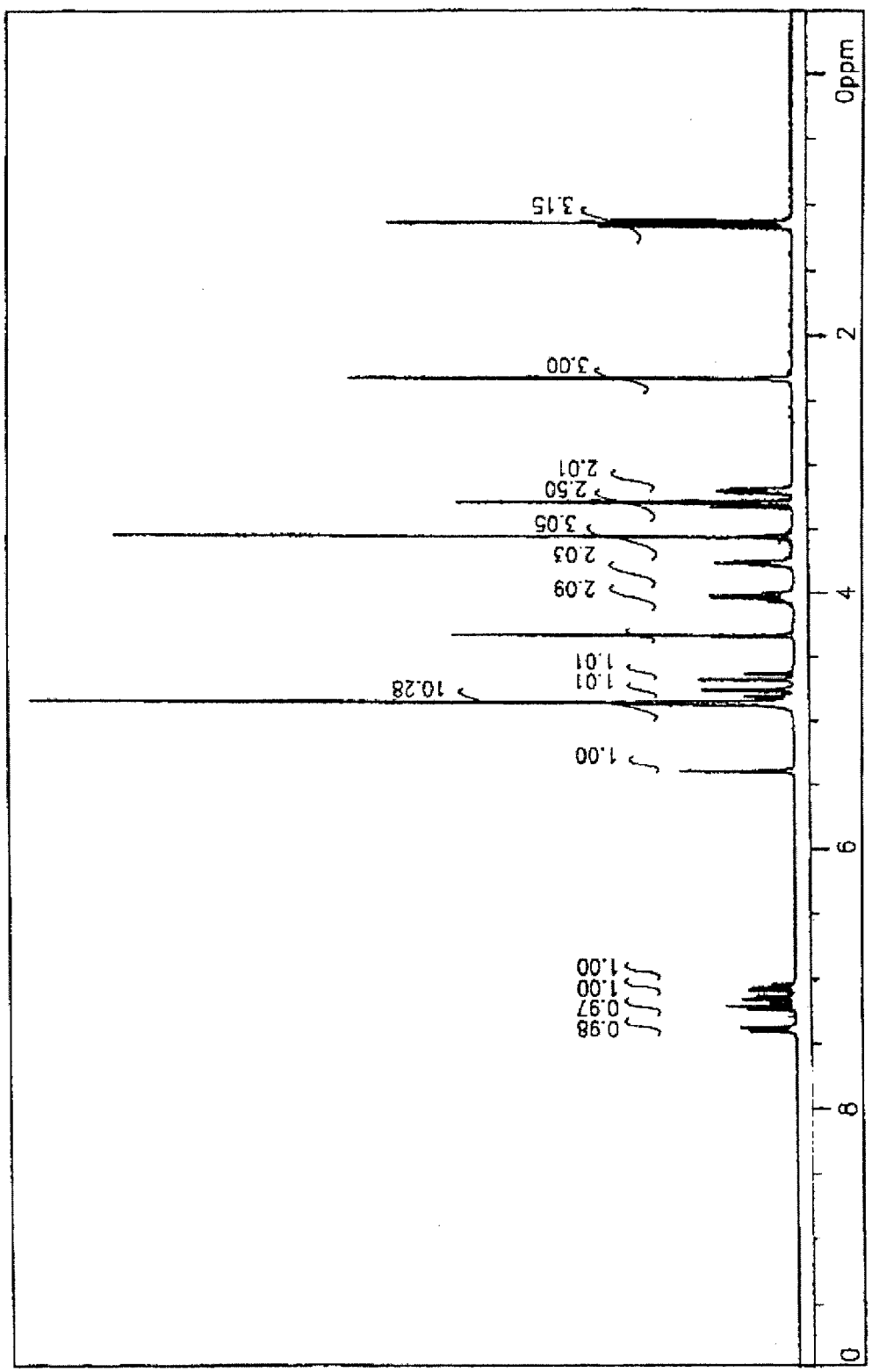
FIG. 2 shows a $^1$H-NMR chart of (S)-(−)-amlodipine-hemi-L-tartrate-monohydrate.

The (S)-(−)-amlodipine-hemi-L-tartrate-DMSO-solvate (5.48 g) obtained in Step (1) was refluxed in methanol (25 ml) to obtain a solution. The solution was cooled to room temperature. The resulting slurry was stirred overnight at room temperature and filtered to obtain a solid. The solid was dried overnight at 50° C. in vacuo to give a solid (4.92 g) having the following $^1$H-NMR data. FIG. 2 shows the $^1$H-NMR chart of the solid, which means that the solid is (S)-(−)-amlodipine-hemi-L-tartrate-monohydrate.

$^1$H-NMR (CD$_3$OD): 7.04-7.41 (m, 4H), 5.40 (s, 1H), 4.72 (gq, 2H), 4.34 (s, 1H), 4.04 (m, 2H), 3.77 (m, 2H), 3.57 (s, 3H), 3.29 (m, 2H), 2.33 (s, 3H), 1.15 (t, 3H)

(3) S-(−)-amlodipine

2N NaHCO$_3$ (44 ml) was added to the slurry of (S)-(−)-amlodipine-hemi-L-tartrate-monohydrate (4.92 g) obtained in Step (2) in $CH_2Cl_2$ (44 ml) at 5° C. The reaction mixture was stirred for 20 minutes. The resulting organic layer was washed with water twice and concentrated. The solution of the resulting mixture in the mixed solvent of 30 ml of n-hexane and ethyl acetate (2:1, v/v) was cooled to 5° C. and filtered. The resulting solid was dried overnight at 50° C. in vacuo to give S-(−)-amlodipine (3.45 g).

Yield: 69%

Melting Point: 108-110° C.

$^1$H-NMR (CD$_3$OD) 7.03-7.41 (m, 4H), 5.39 (s, 1H), 4.67 (gq, 2H), 3.98-4.06 (m, 2H), 3.55-3.58 (t, 2H), 3.57 (s, 3H), 2.86 (m, 2H), 2.33 (s, 3H), 1.15 (t, 3H)

$[\alpha]_D^{25}$=−31.2 (c=1, MeOH)

Chiral HPLC: 97.9% e.e.

EXAMPLE 2

The procedure of Step (3) in Example 1 was repeated, except that (S)-(−)-amlodipine-hemi-L-tartrate-DMSO-solvate (3 g) prepared in accordance with Step (1) of Example 1 was used instead of (S)-(−)-amlodipine-hemi-L-tartrate-monohydrate, to obtain 2.1 g of S-(−)-amlodipine.

$[\alpha]_D^{25}$=−26.4 (c=1, MeOH)

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. (S)-(−)-amlodipine-hemi-L-tartrate-1/4-DMSO-solvate.

* * * * *